US00PP29304P2

(12) United States Plant Patent
Dark

(10) Patent No.: US PP29,304 P2
(45) Date of Patent: May 22, 2018

(54) ***GARDENIA* PLANT NAMED 'PRINCE CHARLES'**

(50) Latin Name: *Gardenia jasminoides*
Varietal Denomination: Prince Charles

(71) Applicant: Thomas Philip Dark, Siler City, NC (US)

(72) Inventor: Thomas Philip Dark, Siler City, NC (US)

( * ) Notice: Subject to any disclaimer, the term of this patent is extended or adjusted under 35 U.S.C. 154(b) by 0 days. days.

(21) Appl. No.: 15/731,001

(22) Filed: Apr. 5, 2017

(51) Int. Cl.
*A01H 5/00* (2018.01)
*A01H 5/02* (2018.01)

(52) U.S. Cl.
USPC ..... Plt./255
CPC ..... *A01H 5/02* (2013.01)

(58) Field of Classification Search
USPC ..... Plt./255
CPC ..... A01H 5/02
See application file for complete search history.

*Primary Examiner* — Kent L Bell
(74) *Attorney, Agent, or Firm* — Samuel R. McCoy, Jr.

(57) ABSTRACT

A new and distinct *Gardenia* cultivar named 'Prince Charles' which is characterized by the combination of a compact and freely-branching growth habit, dense foliage, recurrent flowering from spring until dormancy, an abundance of white double flowers with a sweet fragrance, and the stability of these characteristics from generation to generation.

4 Drawing Sheets

Latin name of the genus and species: The Latin name of the genus and species of the novel variety disclosed herein is *Gardenia jasminoides*.

Variety denomination: The inventive cultivar of *Gardenia* disclosed herein has been given the variety denomination 'Prince Charles'.

BACKGROUND OF THE INVENTION

Parentage: 'Prince Charles' is a seedling selection resulting from the open pollination of a cultivated population of *Gardenia jasminoides* 'Chuck Hayes' (U.S. Plant Pat. No. 28,755) at a commercial plant nursery in Siler City, N.C. In October of 2005, seed was collected from these 'Chuck Hayes' plants, germinated, and the seedlings grown to a mature size in one gallon nursery containers in order to evaluate the progeny for unique characteristics which may be of commercial value. In March of 2006, one such seedling was observed to exhibit early flowering and recurrent flowering through summer, compared to the parent plant which bloomed later and aborted flowers in the heat of summer. The plant was isolated for further evaluation and given the name, 'Prince Charles'.

Asexual Reproduction: Asexual reproduction of 'Prince Charles', by way of softwood stem tip cuttings, was first performed in 2013 in Siler City, N.C. Through four subsequent generations, the unique features of this cultivar have proven to be stable and true to type.

SUMMARY OF THE INVENTION

The cultivar 'Prince Charles' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Prince Charles'. These characteristics in combination distinguish 'Prince Charles' as a new and distinct *Gardenia* hybrid cultivar:

1. *Gardenia* 'Prince Charles' is a compact, freely-branching evergreen shrub with a mounding growth habit; and
2. *Gardenia* 'Prince Charles' exhibits dark green, glossy foliage; and
3. *Gardenia* 'Prince Charles' exhibits recurrent flowering from spring until dormancy; and
4. *Gardenia* 'Prince Charles' does not abort flower buds due to heat stress; and
5. *Gardenia* 'Prince Charles' exhibits an abundance of white double flowers with a sweet fragrance.

BOTANICAL DESCRIPTION OF THE PLANT

Figure 1:
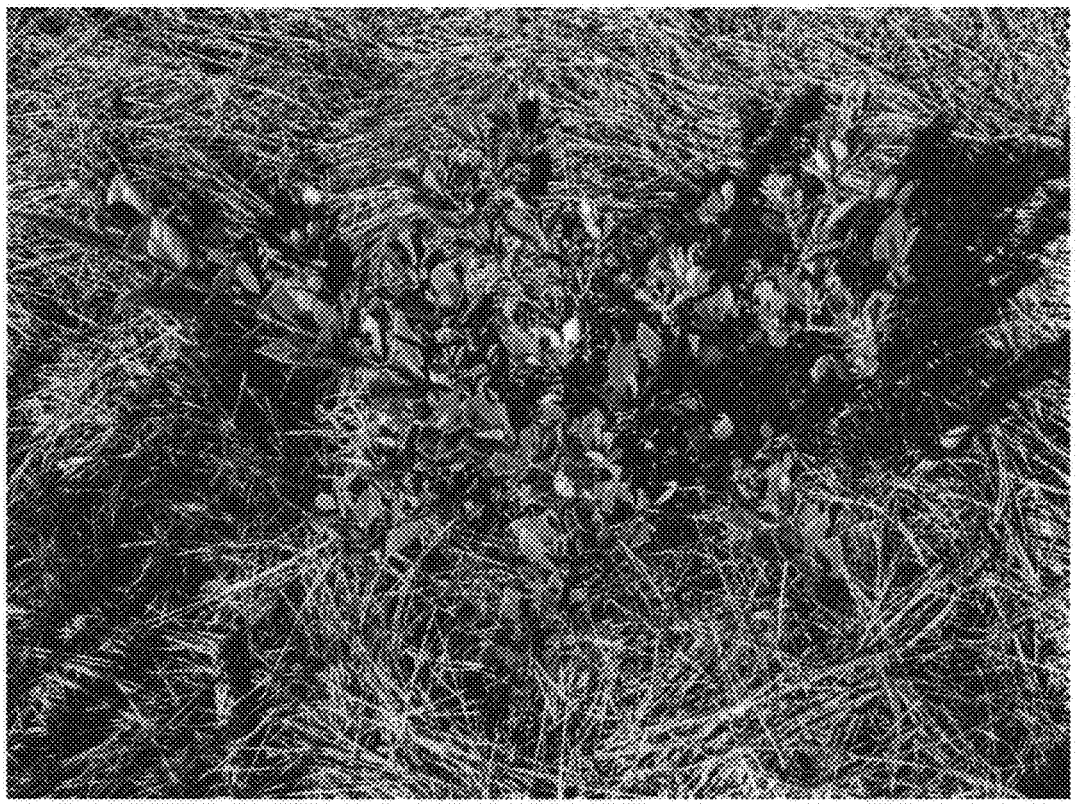
FIG. 1 illustrates, as nearly true as it is reasonably possible to make the same in color photographs of this type, an exemplary 'Prince Charles' plant at approximately 3 years old, grown outdoors in Siler City, N.C.
Figure 2:
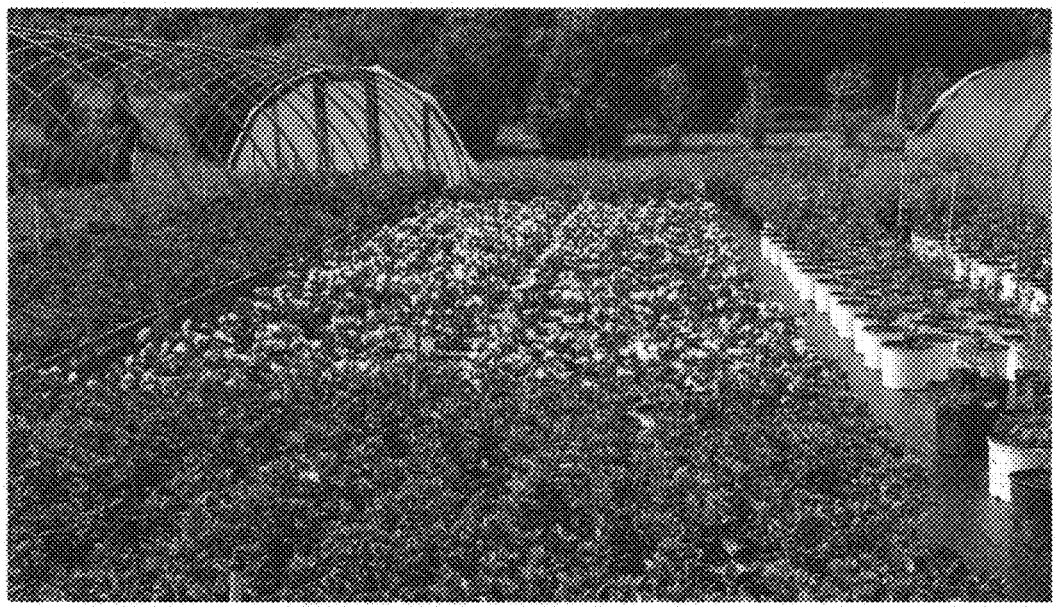
FIG. 2 illustrates, as nearly true as it is reasonably possible to make the same in color photographs of this type, a comparison between a population of 'Prince Charles' plants at approximately 1.25 years old (center) and various other *Gardenia* varieties of like age surrounding said population (left, right, front and rear of photograph). The photograph was taken in late May and illustrates the early season blooming habit. Plants were grown outdoors in Siler City, N.C.
Figure 3:
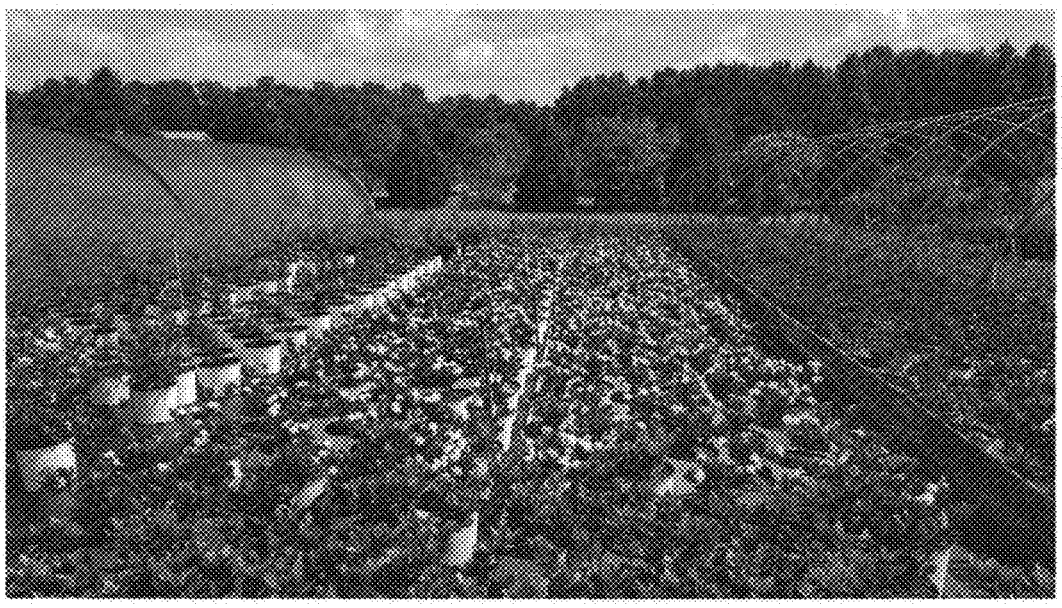
FIG. 3 illustrates, as nearly true as it is reasonably possible to make the same in color photographs of this type, a comparison between a population of 'Prince Charles' plants at approximately 1.5 years old (center) and various other *Gardenia* varieties of like age surrounding said population (left, right, front and rear of photograph). The photograph was taken in late August and illustrates the summer blooming habit. Plants were grown outdoors in Siler City, N.C.
Figure 4:
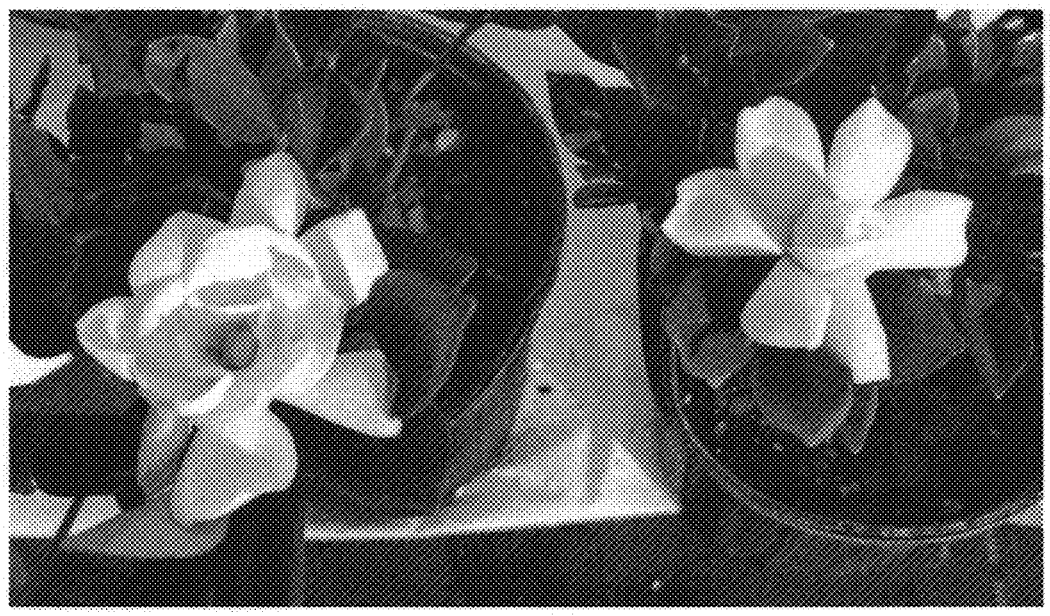
FIG. 4 illustrates, as nearly true as it is reasonably possible to make the same in color photographs of this type, an exemplary flower of 'Prince Charles' when opening (right) and when fully opened (left).

The following observations and measurements made in November of 2016 and, unless otherwise indicated, describe a one year old potted 'Prince Charles' plant grown outdoors in Siler City, N.C. Plants were grown using best management practices for the production of *Gardenia* sp., which consisted of overhead irrigation, 3 times daily, and a fertilizer application of a 9 to 12 month slow release fertilizer. No chemical pest or disease measures were utilized in production. Those skilled in the art will appreciate that certain characteristics will vary with older or, conversely, with younger plants. 'Prince Charles' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 1986 edition.

A botanical description of 'Prince Charles' and comparisons with the parent plant and most similar commercial *Gardenia* cultivar known to the inventor are provided below.

Plant description:

*Growth habit*.—Evergreen flowering shrub with a mounding growth habit.

*Plant shape*.—Globular.

*Average height*.—Approximately 35 cm as observed; 125 cm when fully matured.

*Average width*.—Approximately 35 cm as observed; 150 cm when fully matured.

*Plant vigor*.—Vigorous.

*Propagation details*.—Asexual propagation may be accomplished by softwood stem cuttings.

*Time to initiate roots*.—Approximately 30 to 45 days are required to initiate roots from a softwood cutting.

*Time to produce a marketable rooted cutting*.—Approximately 6 to 8 weeks when propagated in the spring.

*Time to produce a marketable finished plant*.—Approximately 5 months in a 1 gallon nursery container.

*Disease and pest resistance or susceptibility*.—'Prince Charles' has been observed to exhibit moderate resistance to whitefly (*Dialeurodes* sp.). Otherwise, neither susceptibility nor resistance to normal diseases and pests of *Gardenia* has been observed.

*Environmental tolerances*.—Adapt to USDA Zones 7a to 10; drought resistant once established; heat tolerant; tolerant of full sun exposure.

Root system:

*General*.—Fibrous; freely branched and moderately dense rooting.

*Distribution in the soil profile*.—Shallow to moderately deep.

*Texture*.—Juvenile roots are fleshy; older roots are woody.

*Color*.—Juvenile roots are nearest to orange-white, RHS 159D; maturing roots are nearest to greyed-orange, RHS 165B; oldest roots are nearest to greyed-orange, RHS 165A.

Stems:

*Branching habit*.—One main stem, itself freely branching, and giving rise to numerous lateral branches. Lateral branches arising from as low as soil level which, as the plant reaches maturity, results in a multi-stemmed plant.

*Main stem*.—Attitude — Erect. Diameter — 10 mm. Color — Grey-brown, RHS 199A. Texture — Exfoliating in stripes; color is brown, nearest to RHS 200B.

*Lateral branches*.—Aspect — Average angle is approximately 45 to 60 degrees from main stem. Cross section — Rounded. Strength — Strong. Length of lateral branches — 22.5 cm. Diameter of lateral branches — Averaging 0.25 cm at the base. Internode length on lateral branches — Ranging from 1.25 to 2.5 cm. Texture, pubescence and luster of lateral branches — Smooth, glabrous, and slightly glossy. Color, juvenile — Yellow-green, RHS 144A, and becoming suffused with Greyed-Brown, RHS 199C. Color, mature — Greyed-Brown, RHS 199C. Color at internodes — Greyed-brown, RHS 199D.

Foliage:

*Arrangement*.—Opposite.

*Attachment*.—Petiolate.

*Division*.—Simple.

*Density of foliage*.—Very dense.

*Lamina*.—Dimensions — 75 mm long and 30 mm wide, on average. Shape — Obovate. Aspect — Upward. Apex — Acuminate. Base — Cuneate. Margin — Entire; slightly to moderately undulated. Pubescence, adaxial surface — Glabrous. Texture and luster of adaxial surface — Smooth and glossy. Pubescence, abaxial surface — Glabrous. Texture and luster of abaxial surface — Smooth and matte to satiny. Color — Juvenile foliage, adaxial surface — Yellow-green, nearest to RHS 146A yet lighter. Juvenile foliage, abaxial surface — Yellow-green, RHS 146D. Mature foliage, adaxial surface — Yellow-green, nearest to RHS 147A yet darker. Mature foliage, abaxial surface — Yellow-green, in between RHS 147B and 147C. Venation — Pattern — Pinnate. Color, adaxial surface — Yellow-green, RHS 144B. Color, abaxial surface — Yellow-green, RHS 144A.

*Petiole*.—Length — 2.5 mm. Width — 2.0 mm. Texture — Glabrous; smooth. Luster — Matte. Color, adaxial surface — Yellow-green, RHS 144A. Color, abaxial surface — Yellow-green, RHS 144A.

Inflorescence:

*Type*.—Flowers are solitary; borne axially.

*Natural flowering season*.—Spring through fall in Siler City, N.C.

*Flowering habit*.—Recurrent.

*Peduncle*.—Attitude — Upright. Cross section — Ovoid; somewhat flattened. Dimensions — 12 mm long and 2.5 mm wide. Color — Yellow-green, nearest to RHS 144A, yet darker than the calyx. Texture — Glabrous, smooth. Strength — Strong.

Flower buds:

*Bud shape*.—Oblong.

*Bud dimensions*.—35 to 40 mm long and 15 mm in diameter.

*Bud color*.—Yellow-green, RHS 154B, and fading to yellow-green, RHS 150C, towards the distal portion of the bud and heavily suffused with white, nearest to RHS 155D.

Flower:

*Flower habit*.—Perfect; complete; double.

*Flower shape*.—Salverform flowers with an outer whorl of 6 true petals fused at the base and several inner whorls comprised of 10 to 12 petaloids.

*Lastingness*.—Flowers persist for approximately 4 to 7 days.

*Persistence*.—Persistent.

*Flower aspect*.—Upward.

*Fragrance*.—Sweet fragrance which intensifies as the flower ages.

*Calyx*.—Calyx shape — Synsepalous, cupped at the base with 6 sepal lobes arranged in a star shape. Calyx dimensions — 15 mm in diameter and 30 mm deep, including sepal lobes. Sepals — Sepal arrangement — Rotate; fused at the base with 6 linear sepal lobes. Number of sepal lobes — 6. Sepal lobe dimensions — 15 mm long and 3.0 mm wide. Sepal lobe margins — Entire; not undulated. Sepal lobe shape — Linear. Sepal lobe apex — Acute. Sepal base — Fused. Sepal texture — Smooth; glabrous. Sepal color, inner surface — Yellow-green, nearest to RHS 144A yet darker. Sepal color, outer surface — Yellow-green, nearest to RHS 144A yet darker.

*Corolla*.—Petal and petaloid arrangement — Rotate with petals arranged in a single outer whorl and petaloids in 2 or 3 inner whorls. Petals — Quantity — 6. Fused or unfused — Fused. Dimensions — Approximately 15 to 20 mm long and 15 mm wide. Shape — Obovate. Apex — Rounded. Base — Attenuate and becoming fused. Aspect — Involute and heavily reflexed. Margin — Entire; highly undulated and involute. Texture — Glabrous. Luster — Matte. Color when opening (upper side) — White, nearest to RHS 155D. Color when opening (under side) — White, nearest to RHS 155D. Color when fully opened (upper side) — White, nearest to RHS 155D. Color when fully opened (under side) — White, nearest to RHS 155D. Color fading to — Yellow, in between RHS 11C and 11D. Petaloids — Quantity — 10 to 12. Fused or unfused — Free. Dimensions — Highly variable; decreasing in size towards the center of the corolla; largest petaloids are 20 to 25 mm long and 15 to 20 mm wide and the smallest are approximately 18 to 20 mm long and 8 mm wide. Shape — Highly variable; obovate to oblong to spatulate. Apex — Generally rounded. Base — Generally attenuate. Aspect — Involute and moderately reflexed to upright near the center of the corolla. Margin — Entire; highly undulated and involute. Texture — Glabrous. Luster — Matte. Color when opening (upper side) — White, nearest to RHS 155D. Color when opening (under side) — White, nearest to RHS 155D. Color when fully opened (upper side) — White, nearest to RHS 155D. Color when fully opened (under side) — White, nearest to RHS 155D. Color fading to — Yellow, in between RHS 11C and 11D.

Reproductive organs:

*Androecium*.—Stamen quantity — 6. Anther — Anther attachment — Adnate. Anther shape — Linear, flattened, with a longitudinal split. Anther size — 15 mm long and 2.0 mm in diameter. Anther color — A mixture of yellow, RHS 11D, and greyed-brown, RHS 199D. Pollen — Amount of pollen — Scarce. Pollen color — Yellow, RHS 9B.

*Gynoecium*.—Pistil quantity — One. Stigma — Shape — Divided into 2 to 4 irregularly sized segments; segments oblong. Dimensions — Approximately 6.0 to 7.0 mm across and 15 mm tall. Color — Yellow, RHS 10A. Style — Dimensions — 10 mm long and 1.75 mm in diameter. Color — Greyed-brown, nearest to RHS 199D yet lighter. Ovary — Position — Inferior. Shape — Elliptical. Dimensions — 3.5 mm long and 4 mm wide. Color — Yellow, RHS 7C.

Seed and fruit: Not observed.

Comparison With the Parent Plant

Plants of the new cultivar 'Prince Charles' may be distinguished from its parent, *Gardenia* 'Chuck Hayes' (U.S. Plant Pat. No. 8,755), by the characteristics described in Table 1.

TABLE 1

Comparison with Parent Plant

| Characteristic | 'Prince Charles' | 'Chuck Hayes' |
|---|---|---|
| Mature plant size. | More compact and more densely foliaged than 'Chuck Hayes' | Larger and more open than 'Prince Charles'. |
| Internode length on lateral branches. | Shorter than 'Chuck Hayes'. | Longer than 'Prince Charles'. |
| Flower habit. | Double. | Single. |
| Bloom habit. | Recurrent blooming from spring until dormancy. | Spring flowering, with intermittent flowering through summer. |

Comparison With the Closest Known Commercial Comparator

Plants of the new cultivar 'Prince Charles' can be distinguished from the commercial variety, *Gardenia* 'MADGA I' (U.S. Plant Pat. No. 19,988), by the characteristics described in Table 2.

TABLE 2

Comparison with Closest Commercial Comparator

| Characteristic | 'Prince Charles' | 'MADGA I' |
|---|---|---|
| Mature plant size. | More compact and more densely foliaged than 'MADGA I'. | Larger and more open than 'Prince Charles'. |

TABLE 2-continued

| Comparison with Closest Commercial Comparator | | |
|---|---|---|
| Characteristic | 'Prince Charles' | 'MADGA I' |
| Internode length on lateral branches. | Shorter than 'MADGA I'. | Longer than 'Prince Charles'. |
| Leaf size. | Smaller than 'MADGA I'. | Larger than 'Prince Charles'. |

TABLE 2-continued

| Comparison with Closest Commercial Comparator | | |
|---|---|---|
| Characteristic | 'Prince Charles' | 'MADGA I' |
| Bloom habit. | Recurrent blooming from spring until dormancy. | Spring with intermittent flowering through summer. |

That which is claimed is:

1. A new and distinct cultivar of *Gardenia* plant named 'Prince Charles', substantially as described and illustrated herein.

* * * * *